United States Patent [19]

Tamura et al.

[11] Patent Number: 5,004,843
[45] Date of Patent: Apr. 2, 1991

[54] PROCESS FOR PRODUCING ALLYLIC ALCOHOLS

[75] Inventors: Mitsuhisa Tamura; Gohu Suzukamo; Ken-ichi Hirose, all of Osaka, Japan

[73] Assignee: Sumitomo Chemical Company, Limited, Osaka, Japan

[21] Appl. No.: 529,730

[22] Filed: May 29, 1990

Related U.S. Application Data

[63] Continuation of Ser. No. 338,546, Apr. 17, 1989, abandoned, which is a continuation of Ser. No. 91,308, Aug. 28, 1987, abandoned, which is a continuation of Ser. No. 430,511, Sep. 30, 1982, abandoned, which is a continuation of Ser. No. 209,143, Nov. 21, 1980, abandoned.

[30] Foreign Application Priority Data

Nov. 22, 1979 [JP] Japan ................. 54-151877
Nov. 22, 1979 [JP] Japan ................. 54-151878
Apr. 8, 1980 [JP] Japan ................. 55-46347
Jun. 13, 1980 [JP] Japan ................. 55-80413
Jun. 25, 1980 [JP] Japan ................. 55-86873

[51] Int. Cl.⁵ .................. C07C 41/00; C07C 33/34; C07C 33/28; C07C 35/06
[52] U.S. Cl. .................. 568/670; 568/675; 568/808; 568/813; 568/817; 568/821; 568/828; 568/838; 568/839; 568/908; 568/909.5; 549/347; 549/350; 549/357; 549/362; 549/430; 549/445; 549/510; 549/512
[58] Field of Search ............. 568/670, 675, 808, 813, 568/817, 821, 828, 838, 839, 908, 909.5; 549/347, 350, 357, 362, 430, 445, 510, 512

[56] References Cited

PUBLICATIONS

Aithie et al., Tetrahedron Letters 49, 4419–4420 (1975).
Anderson, J. Amer. Chem. Soc. 92, 4978–4979 (1970).
Herr et al., J. Amer. Chem. Soc. 92, 4979–4981 (1970).
J. of Am. Chem. Soc., 95, 957 (1973).
J. Am. Chem. Soc., 92, 226 (1970).
Tetrahedron Letters, 1975, 4419.
Aithie et al., Tetrahedron Letters, 1975, 4419.

*Primary Examiner*—Alan Siegel
*Attorney, Agent, or Firm*—Birch, Stewart, Kolasch & Birch

[57] ABSTRACT

Process for preparing predominantly Z-substituted allylic alcohols of the formula:

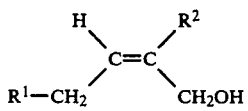

wherein $R^1$ is a straight or branched $C_1$–$C_{25}$ alkyl group optionally bearing at least one substituent and/or at least one unsaturated linkage and $R^2$ is a hydrogen atom or a methyl group, which comprises reacting a vinyl epoxide of the formula:

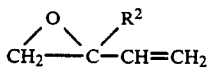

wherein $R^2$ is as defined above with an organolithium compound of the formula above. More particularly, there is disclosed a process for $R^1$—Li wherein $R^1$ is as defined above; particularly, process for preparing α-santalol of the formula:

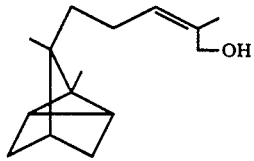

which comprises reacting 3-methyl-3,4-epoxybutene-1 with lithiomethyl-2,3-dimethyltricyclo[2.2.1.0²,⁶]heptane.

15 Claims, No Drawings

PROCESS FOR PRODUCING ALLYLIC ALCOHOLS

This application is a continuation of application Ser. No. 338,546 filed Apr. 17, 1989 now abandoned which is a continuation of Ser. No. 091,308 filed Aug. 28, 1987 now abandoned which is a continuation of Ser. No. 430,511 filed Sep. 30, 1982 now abandoned which is a continuation of Ser. No. 209,143 filed Nov. 21, 1980 now abandoned.

The present invention relates to a process for producing allylic alcohols. More particularly, it relates to a process for producing selectively Z-substituted allylic alcohols of the formula:

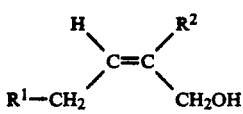

wherein $R^1$ is a straight or branched $C_1-C_{25}$ alkyl group optionally bearing at least one substituent and/or at least one unsaturated linkage (except an $\alpha,\beta$-unsaturated linkage) and $R^2$ is a hydrogen atom or a methyl group. The term "alkyl" as herein used is intended to mean not only an acyclic one but also a cyclic one.

Examples of the alkyl group represented by the symbol $R^1$ are methyl, ethyl, n-propyl, n-butyl, n-pentyl, n-hexyl, n-heptyl, n-octyl, isopropyl, isobutyl, sec-butyl, t-butyl, 2-methylbutyl, 3-methylbutyl, 3,7,11-trimethyldodecyl, 3,7,11,15-tetramethylhexadecyl, 4-pentenyl, 3,7-dimethyl-6-octenyl, cyclopropyl, cyclobutyl, cyclopentyl, cyclohexyl, 4-methylcyclohexyl, (2,3-dimethyltricyclo [2.2.1.0$^{2,6}$]heptyl-3-)methyl, (2-methyl-3-methylenenorbornyl-2-)methyl, 2,2-ethylenedioxy-1,7-dimethylbicyclo[2.2.1]-heptyl-7-methyl, etc. Examples of the substituent(s) which may be present on these alkyl groups are in aromatic hydrocarbon group (e.g. phenyl, naphthyl) (except $\alpha$-substitution), lower alkoxy, lower alkylenedioxy, etc. The aromatic hydrocarbon group may further bear lower alkyl, lower alkoxy, etc. Thus, $R^1$ can include alkyl (including cycloalkyl), alkenyl (including cycloalkenyl) (except $\alpha,\beta$-unsaturated alkenyl), aralkyl (e.g. 2-phenylethyl, 2-(naphthyl-1-)ethyl) (except $\alpha$-substitution), etc.

The Z-substituted allylic alcohols (I) include the following two groups:

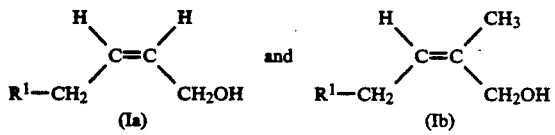

wherein $R^1$ is as defined above. For preparation of these Z-substituted allylic alcohols, there are known the following procedures:

(a) Reaction of mono-substituted acetylenes with n-butyllithium and formaldehyde and partial hydrogenation of the resulting hydroxymethylated compounds with hydrogen in the presence of a Lindlar catalyst;

(b) Reaction of heptyl aldehyde with a Wittig's reagent, followed by reaction of the product with n-butyllithium and formaldehyde (J. Am. Chem. Soc., 92, 226 (1970);

(c) Reaction of 2-methyl-4-substituted buten-2-yl chlorides with sodium acetate, followed by hydrolysis of the resulting acetates (Bull. Soc. Chim. Fr., 1973, 3065);

(d) Reaction of 3-methyl-3,4-epoxybutene-1 with phenyllithium (Tetrahedron Letters, 1975, 4419);

(e) Reduction of vinyl epoxides with diisobutylaluminum hydride (J. Am. Chem. Soc., 95, 957 (1973)), etc.

However, none of these conventional procedures is suitable for selective production of the Z-substituted allylic alcohols (I) on an industrial scale, because its applicability is quite restricted, indispensable multi-steps are required, the reaction procedure is complicated, an extremely low temperature around $-80°$ C. is needed, the use of an expensive reagent is essential, the starting material is not readily available on the market, etc.

As the result of an extensive study, it has now been found that the reaction of 3,4-epoxybutene-1 or 3-methyl-3,4-epoxybutene-1 with an organolithium compound, particularly in the presence of a base, can afford the Z-substituted allylic alcohol (I) in a single step with a good yield. Advantageously, the reaction conditions are mild and the reaction operation is quite simple. It is particularly notable that the objective compound is obtainable with a high regioselectivity and a high stereoselectivity.

According to the present invention, there is provided a process for preparing predominantly Z-substituted allylic alcohols (I) which comprises reacting a vinyl epoxide of the formula:

wherein $R^2$ is as defined above with an organolithium compound of the formula:

wherein $R^1$ is as defined above.

The process of this invention can afford the Z-substituted allylic alcohol (I) as the main product. When a base is present in the reaction system, the stereoselectivity thereto is more enhanced.

The starting vinyl epoxide (II: $R^2$=hydrogen) can be obtained by oxidation of butadiene with a peroxide by converting butadiene into 1-halo-2-hydroxybutene-3, followed by treatment with a base. The starting vinyl epoxide (II: $R^2$=methyl) may be produced from 2-methylbutadiene in substantially the same procedure as above.

The organolithium compound (III) is obtainable by reacting the corresponding organic halide of the formula: $R^1X$ wherein $R^1$ is as defined above and X is a halogen atom with lithium metal.

In carrying out the process of this invention, the vinyl epoxide (II) is reacted with the organolithium compound (III), usually in a molar proportion of 1:0.1–100 preferably of around 1:1.

The reaction is normally effected in an inert solvent under the atmosphere of an inert gas (e.g. nitrogen, argon, helium). Examples of the inert solvent are a hydrocarbon (e.g. pentane, hexane, heptane, benzene, toluene), an ether (e.g. diethyl ether, 1,4-dioxane, tetrahydrofuran, dimethoxyethane), etc. These solvents may be used alone in combination. The amount of the inert solvent may be usually from 0.1 to 50 liters per 1 mol of the vinyl epoxide (II).

The reaction temperature may be usually not higher than the refluxing temperature of the reaction mixture, preferably between −30° C. and ordinary temperature (e.g. 30° C.). The reaction time is not limitative and may be generally from 5 minutes to 10 hours.

In order to enhance the stereoselectivity to the Z-substituted allylic alcohol (I), the presence of an amine or a metal alkoxide as a base in the reaction system is preferred. As the amine, there may be employed any one of primary, secondary and tertiary amines. Specific examples are ammonia, methylamine, dimethylamine, trimethylamine, ethylamine, diethylamine, triethylamine, propylamine, dipropylamine, tripropylamine, butylamine, dibutylamine, tributylamine, pentylamine, dipentylamine, tripentylamine, hexylamine, dihexylamine, trihexylamine, octylamine, dioctylamine, trioctylamine, decylamine, didecylamine, tridecylamine, cyclopropylamine, cyclobutylamine, cyclopentylamine, cyclohexylamine, dimethyloctylamine, dimethyldecylamine, dimethyllaurylamine, dimethylcoconutamine, dimethylmyristylamine, dimethylpalmitylamine, dimethylstearylamine, dimethyloleylamine, (S)-2-(anilinomethyl)pyrrolidine, (S)-2-(N-methyl-N-phenylaminomethyl)-N'-methylpyrrolidine, spaltene, aniline, N-methylaniline, N,N-dimethylaniline, toluidine, diphenylamine, triphenylamine, pyrrole, N-methylpyrrole, piperidine, N-methylpiperidine, morpholine, N-methylmorpholine, ethylenediamine, N,N,N',N'-tetramethylethylenediamine, N,N,N',N'-tetraethylethylenediamine, N,N,N',N'-tetramethyldiaminopropane, N,N,N',N'-tetramethyldiaminobutane, N,N,N',N'-tetramethyldiaminohexane, N,N,N',N'-tetramethylphenylenediamine, N,N,N',N'',N''-pentamethyldiethylene triamine, 1,4-diazabicyclo[2.2.2]octane, 1,5-diazabicyclo[5.4.0]undecene-5, 1,5-diazabicyclo[4.3.0]nonene-5, etc. Among them, tertiary amines are preferred from the economical viewpoint. The amount of the amine may be not less than 0.05 mol per one mole of the organolithium compound (III). When the amine is a liquid, it may be used in a large excessive amount so as to serve itself as the reaction medium. In such case, the use of any other inert solvent may be omitted. Examples of the liquid amine are triethylamine, tripropylamine, tributylamine, N,N,N',N'-tetramethylethylenediamine, etc.

As the metal alkoxide, there may be employed the compound of the formula: $R^3OM$ wherein $R^3$ is lower alkyl (e.g. methyl, ethyl, n-propyl, n-butyl, n-pentyl, n-hexyl, n-heptyl, n-octyl, iso-propyl, iso-butyl, sec-butyl, t-butyl, 2-methylbutyl, 3-methylbutyl, cyclohexyl), lower alkenyl (e.g. allyl), ar(lower)alkyl (e.g. benzyl, phenethyl) or the like and M is lithium, sodium, potassium, or the like. The metal alkoxide may be prepared from the corresponding alcohol and the corresponding metal or its compound in the reaction system. In the alternative, the metal alkoxide as prepared previously and separately may be introduced into the reaction system. The amount of the metal alkoxide is usually not less than 5 mol % with respect to the organolithium compound (III).

Recovery of the reaction produce from the reaction mixture may be accomplished by a per se conventional procedure. For instance, the reaction mixture is admixed with a saturated ammonium chloride solution under cooling with ice water and extracted with a solvent such as ether or heptane. Removal of the solvent from the extract under reduced pressure gives the objective Z-substituted allylic alcohol (I), which does not substantially contain any by-product such as the 1,2-addition product. For further purification, there may be adopted distillation, column chromatography of the like.

The Z-substituted allylic alcohols (I) prepared by the process of this invention are useful for the synthesis of pharmaceuticals, agro-chemicals, perfumes, or their intermediates, etc. For instance, α-santalol and β-santalol which are man constituents of East Indian sandalwood oil are such examples. Thus, α-santalol can be produced according to the following scheme including the process of this invention:

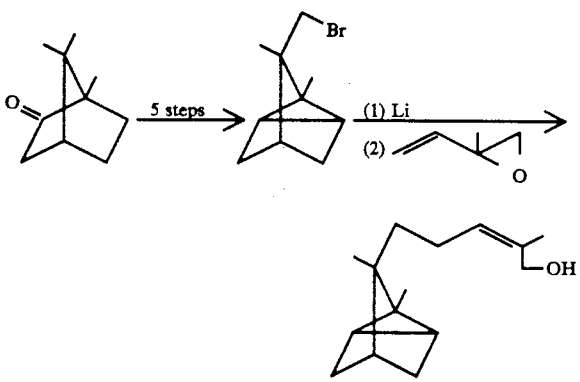

In the above scheme, the use of d-camphor as the starting material can afford α-santalol having the same configuration as that of natural α-santalol.

Among the Z-substituted allylic alcohols (I), those of the formula:

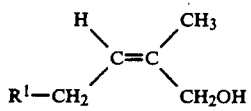

wherein $R^1$ is sec-butyl, iso-butyl, cyclopropyl, cyclohexyl, 2-phenylethyl or 2,2-ethylenedioxy-1,7-dimethylbicyclo[2.2.1]heptyl-7-methyl are novel.

Practical and presently preferred embodiments of this invention are illustratively shown in the following Examples.

EXAMPLE 1

3-Lithiomethyl-2,3-dimethyltricyclo[2.2.1.0$^{2,6}$]heptane was prepared from 115 mg of 30% lithium dispersion (containing 2% sodium) and 225 mg of 3-bromomethyl-2,3-dimethyltricyclo[2.2.1.0$^{2,6}$]heptane (i.e. π-bromotricyclene) $[\alpha]_D = -9.81°$) in an ether/pentane mixed solvent under an argon atmosphere. To the reaction mixture, there was dropwise added 243 mg of N,N,N',N'-teramethylethylenediamine (hereinafter referred to as "TMEDA") dissolved in pentane (1.5 ml) at 0° C. A solution of 85 mg of 3-methyl-3,4-epoxybutene-1 in pentane (1 ml) was further added dropwise thereto and, after the addition was completed, the mixture was stirred at 0° C. for 50 minutes and at room temperature for 30 minutes. The reaction mixture was re-cooled to 0° C., and after adding saturated ammonium chloride solution thereto, extracted with ether.

The ether extract was washed with saturated sodium chloride solution and dried over anhydrous magnesium sulfate. Removal of the solvent gave an oily yellow product and purification by column chromatography on silica gel gave 133 mg of α-santalol (yield, 58%; Z/E=94.7/5.3).

This produce was further subjected to purification by column chromatography on silica gel to obtain pure α-santalol of Z-configuration, which gave $[\alpha]_D = +17.6°$ (C=1.0, CHCl$_3$).

NMR spectrum (CDCl$_3$) δ ppm: 5.36 (1H, triplet), 4.18 (2H, singlet), 1.80 (3H, singlet), 0.98 (3H, singlet), 0.82 (3H, singlet), 2.2–0.8 (12H, multiplet).

EXAMPLE 2

3-Lithiomethyl-2,3-dimethyltricyclo[2.2.1.0$^{2,6}$]heptane was prepared from 107 mg of 30% lithium dispersion (containing 2% sodium) and 225 mg of 3-bromomethyl-2,3-dimethyltricyclo[2.2.1.0$^{2,6}$]heptane in an ether/hexane mixed solution under an argon atmosphere. After cooling the resulting solution to 0° C., 92 mg of 3-methyl-3,4-epoxybutene-1 dissolved in ether was added dropwise thereto. The reaction mixture was stirred at 0° C. for 1 hour, and after being gradually raised to room temperature, stirred at room temperature for ¼ hour. The reaction mixture was recooled to 0° C., excess lithium was treated with ethanol and water, and then work up was carried out as usual. Purification by column chromatography on silica gel gave 140 mg of α-santalol (yield, 61%; Z/E=87.5/12.5).

EXAMPLE 3

Reaction and work up were carried out in the same manner as in Example 2 except that 169 mg of 3-chloromethyl-2,3-dimethyltricyclo[2.2.1.0$^{2,6}$]heptane was used in place of 3-bromomethyl-2,3-dimethyltricyclo[2.2.1.0$^{2,6}$]heptane, and 68 mg of α-santalol was thus obtained. This produce was mainly of Z-isomer and contained only a trace amount of E-isomer.

EXAMPLE 4

7-Lithiomethyl-2,2-ethylenedioxy-1,7-dimethylbicyclo[2.2.1]heptane was prepared from 238 mg of 30% lithium dispersion and 262 mg of 7-bromomethyl-2,2-ethylenedioxy-1,7-dimethylbicyclo[2.2.1]heptane in an ether/hexane mixed solvent under a nitrogen atmosphere. After cooling the resulting mixture to −30° C., 93 mg of 3-methyl-3,4-epoxy-butene-1 dissolved in ether was added dropwise thereto. The mixed solution was stirred at −30° C. for 2 hours, and after being gradually raised to room temperature, stirred at room temperature for 1 hour. The reaction mixture was recooled to 0° C., excess lithium was treated with ethanol and water, and then work up was carried out as usual. Thereafter, purification by column chromatography on silica gel gave 14 mg of 7-(2-methyl-2-penten-1-ol-5-yl)-2,2-ethylenedioxy-1,2dimethylbicyclo[2.2.1]heptane (yield, 54% based on 7-bromomethyl-2,2-ethylenedioxy-1,7-dimethylbicyclo[2.2.1]-heptane used). The Z/E ratio of this product was 90.4/9.6.

NMR spectrum (CDCl$_3$) δ ppm: 5.32 (1H, triplet), 4.10 (2H, singlet), 3.83 (4H, multiplet), 1.78 (3H, broad singlet), 1.03 (3H, singlet), 0.77 (3H, singlet), 2.3–0.2 (12H, multiplet).

EXAMPLE 5

A hexane solution of n-butyllithium (2.1 mmol) was cooled to 0° C. under an argon atmosphere, and a hexane solution of n-butanol (74 mg; 1.0 mmol) was added dropwise thereto and stirred. A hexane solution of 3-methyl-3,4-epoxybutene-1 (84.4 mg; 1.0 mmol) was further added thereto, and after the addition was completed, the reaction mixture was stirred at 0° C. for 1 hour and at room temperature for 1 hour, followed by the usual work up. Removal of the solvent and distillation of the residue gave 104 mg of 2-methyl-2-octen-1-ol (yield, 73%). NMR spectrum and gas chromatographic analysis (Golay column, PEG 20M, 45 m, at 140°) showed that the resulting product contained none of 3-methyl-1-octen-4-ol, 2-methyl-2-vinylhexen-1-ol, 3-methyl-1-octen-3-ol, etc. The Z/E ratio of 2-methyl-2-octen-1-ol was 97.2/2.8.

NMR spectrum (CCl$_4$) δ ppm: Z-isomer: 5.23 (1H, triplet), 4.03 (2H, singlet), 3.33 (1H, singlet), 1.75 (3H, singlet), 2.25–0.6 (11H, multiplet); E-isomer: 5.37 (1H, triplet), 3.90 (2H, singlet), 3.33 (1H, singlet), 1.63 (3H, singlet), 2.25–0.6 (11H, multiplet).

The $^{13}$C-NMR spectral data of 2-methyl-2-octen-1-ol was as follows: CDCl$_3$δ ppm: Z-isomer: 61.5 (C-1), 134.3 (C-2), 128.7 (C-3), 27.6 (C-4), 29.8 (C-5), 31.6 (C-6), 22.6 (C-7), 14.0 (C-8), 21.2 (C-9), when the carbon atoms were numbered in the following manner:

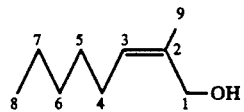

In $^1$H-NOE experiment of the reaction product (Z/E=95/5), irradiation of H-4 proton in the major component increased the intensity of H-1 (30%) and irradiation of H-3 proton in the minor component increased the intensity of H-1 (21%). Thus, the major and minor component were assigned to the Z- and E-configuration, respectively.

EXAMPLES 6 and 7

Reaction and work up were carried out in the same manner as in Example 5 except that the amounts of n-butanol and n-butyllithium were varied. The results are shown in Table 1.

TABLE 1

| Example | Molar ratio (A)*$^1$ | Molar ratio (B)*$^2$ | Yield (%) | Z/E |
|---|---|---|---|---|
| 6 | 0.12 | 1.2 | 67 | 92.0/8.0 |
| 7 | 5.2 | 6.3 | 59 | 97.3/2.7 |

Note:
*$^1$The molar ratio (A) refers to that of n-butanol to 3-methyl-3,4-epoxy-butene-1.
*$^2$The molar ratio (B) refers to that of n-butyllithium to 3-methyl-3,4-epoxybutene-1.

EXAMPLES 8 to 10

Reaction and work up were carried out in the same manner as in Example 5 except that n-butanol was replaced by any other alcohol as shown in Table 2. The results are also shown in Table 2.

TABLE 2

| Example | Alcohol | Molar ratio (A)*$^1$ | Molar ratio (B)*$^2$ | Yield (%) | Z/E |
|---|---|---|---|---|---|
| 8 | iso-Butanol | 1.0 | 2.1 | 71 | 91.1/8.9 |
| 9 | sec-Butanol | 1.0 | 2.2 | 68 | 89.2/10.8 |

TABLE 2-continued

| Example | Alcohol | Molar ratio (A)[*1] | Molar ratio (B)[*2] | Yield (%) | Z/E |
|---------|---------|---------------------|---------------------|-----------|-----|
| 10 | n-Octanol | 1.0 | 2.2 | 65 | 95.2/4.8 |

Note:
[*1]The molar ratio (A) refers to that of alcohol to 3-methyl-3,4-epoxybutene-1.
[*2]The molar ratio (B) refers to that of n-butyllithium to 3-methyl-3,4-epoxybutene-1.

EXAMPLES 11 TO 14

Reaction and work up were carried out in the same manner as in Example 5 except that n-butyllithium and n-butanol were replaced by any other organolithium compound and any other alcohol as shown in Table 3. The results are also shown in Table 3.

TABLE 3

| Example | Organolithium compound | Alcohol | Molar ratio (A)[*1] | Molar ratio (B)[*2] | Yield (%) | Z/E |
|---------|------------------------|---------|---------------------|---------------------|-----------|-----|
| 11 | sec-Butyllithium | n-Butanol | 1.0 | 2.2 | 51 | 97.8/2.21 |
| 12 | sec-Butyllithium | sec-Butanol | 0.9 | 2.1 | 49 | 96.0/4.09 |
| 13 | sec-Butyllithium | iso-Butanol | 1.0 | 2.1 | 51 | 97.4/2.61 |
| 14 | sec-Butyllithium | t-Butanol | 1.0 | 2.2 | 56 | 91.8/8.26 |

Note:
[*1]The molar ratio (A) refers to that of alcohol to 3-methyl-3,4-epoxybutene-1.
[*2]The molar ratio (B) refers to that of sec-butyllithium to 3-methyl-3,4-epoxybutene-1.

NMR spectrum (CDCl$_3$) δ ppm: Z-isomer: 5.30 (1H, triplet), 4.10 (2H, singlet), 2.1–0.6 (15H, multiplet); E-isomer: 5.42 (1H, triplet), 3.98 (2H, singlet), 2.1–0.6 (15H, multiplet).

EXAMPLE 15

A hexane solution of n-butanol (77.1 mg; 1.0 mmol) was cooled to 0° C. under an argon atmosphere, and a hexane solution of n-butyllithium (1.0 ml) was added dropwise thereto and stirred. To the resulting solution, there was further dropwise added a hexane solution of n-octyllithium (1.2 mmol) and a hexane solution of 3-methyl-3,4-epoxybutene-1 (88.1 mg; 1.0 mmol), and after the addition was completed, the resulting mixture was cooled at 0° C. for 1 hour and at room temperature for 1.5 hours, followed by the usual work up. Removal of the solvent and distillation of the residue gave 150 mg of 2-methyl-2-dodecen-1-ol (yield, 75%; Z/E=93.0/7.0).

NMR spectrum (CDCl$_3$) δ ppm: Z-isomer: 5.22 (1H, triplet, J=7.3 hz), 4.05 (2H, singlet), 1.78 (3H, singlet), 2.3–0.7 (20H, multiplet).

EXAMPLE 16

To 85.6 mg (1.1 mmol) of lithium butoxide prepared from n-butanol and lithium metal, there was added 10 ml of ether under an argon atmosphere and stirred at room temperature. The resulting mixture was cooled to −20° C., and a hexane solution of n-butyllithium (1.2 mmol) was added thereto and stirred. An ether solution of 3-methyl-3,4-epoxybutene-1 (89.9 mg; 1.1 mmol) was added dropwise thereto at −20° C., and after the addition was completed, stirring was effected at −20° C. for 1 hour and at 0° C. for 1 hour, followed by the usual work up to give 2-methyl-2-octen-1-ol in a yield of 74%. The Z/E ratio was 93.1/6.9.

EXAMPLE 17

A hexane solution of n-butyllithium (2.1 mmol) was cooled at 0° C. under the argon atmosphere. A hexane solution of n-butanol (75.9 mg; 1.0 mmol) was added dropwise thereto and stirred. To the resulting solution, there was further added dropwise a hexane solution of 3,4-epoxy-butene-1 (70.0 mg; 1 mmol), and after the addition was completed, the resulting mixture was cooled at 0° C. for 1 hour and at room temperature for 30 minutes, followed by the usual work up. Removal of the solvent and distillation of the residue gave 63 mg of 2-octen-1-ol (yield, 49%). After acetylation of the thus obtained product, gas chromatographic analysis (PEG 20M, 4 m) was effected at a temperature of 130° C. The retention times of Z-isomer and E-isomer were respectively 13.7 minutes and 14.7 minutes, and the Z/E ratio was 89.1/10.9.

NMR spectrum (CDCl$_3$) δ ppm: Z-acetate: 5.59 (2H, multiplet), 4.62 (2H, doublet, J=5.4 Hz), 2.60 (3H, singlet), 2.06 (2H, multiplet), 1.31 (6H, multiplet), 0.89 (3H, multiplet); E-acetate: 5.66 (2H, multiplet), 4.50 (2H, doublet, J=5.6 Hz), 2.06 (3H, singlet), 2.06 (2H, multiplet), 1.31 (6H, multiplet), 0.89 (3H, multiplet).

The $^{13}$NMR spectral data of 9-octen-1-ol was as follows: (CDCl$_3$) δ ppm: Z-acetate: 60.4 (C-1), 135.4 (C-2), 123.4 (C-3), 27.5 (C-4), 29.1 (C-5), 31.4 (C-6), 22.5 (C-7), 14.0 (C-8); E-acetate: 65.2 (C-1), 136.6 (C-2), 123.9 (C-3), 33.2 (C-4), 28.6 (C-5), 31.4 (C-6), 22.5 (C-7), 13.9 (C-8), when the carbon atoms were numbered in the following manner:

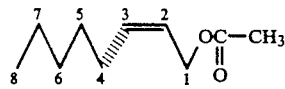

EXAMPLE 18

A solution of 283 mg of TMEDA in 1.5 ml of hexane was cooled to 0° C., and a hexane solution of n-butyllithium (1.25 mmol) was added dropwise thereto under a nitrogen atmosphere and stirred at 0° C. To the resultant mixture, there was added dropwise a hexane solution of 3-methyl-3,4-epoxybutene-1 (91 mg; 1.1 mmol). After completion of the addition, the resultant mixture was stirred at 0° C. for hours and at room temperature for 1 hour, followed by the usual work up. After removal of the solvent, the residue was distilled off to give 105 mg of 2-methyl-2-octen-1-ol as a colorless product (yield, 68%; Z/E=95.5/4.5).

EXAMPLES 19 TO 26

Reaction and work up were carried out in the same manner as in Example 18 except that the molar ratio of the added TMEDA, the reaction temperature and the solvent were varied. The results are shown in Table 4.

TABLE 4

| Example | Molar ratio of TMEDA[*1] | Solvent | Temperature (°C.) | Yield[*2] (%) | Z/E |
|---------|--------------------------|---------|-------------------|---------------|-----|
| 19 | 0.09 | Hexane | 0 | 67 | 89.4/10.6 |
| 20 | 0.49 | Hexane | 0 | 64 | 91.6/8.4 |
| 21 | 1.0 | Hexane | 0 | 78 | 93.5/6.5 |
| 22 | 13.1 | TMEDA | 0 | 74 | 95.0/5.0 |
| 23 | 1.0 | Hexane | −50 | 75 | 94.6/5.4 |
| 24 | 1.0 | Ether | −20 | 74 | 93.4/6.6 |
| 25 | 1.0 | Benzene | 10 | 71 | 90.9/9.1 |

TABLE 4-continued

| Example | Molar ratio of TMEDA*1 | Solvent | Temperature (°C.) | Yield*2 (%) | Z/E |
|---|---|---|---|---|---|
| 26 | 1.0 | Tetrahydrofuran | −30 | 63 | 86.3/13.7 |

Note:
*1 The molar ratio refers to that of TMEDA to n-butyllithium.
*2 The yield refers to that of 2-methyl-2-octen-1-ol isolated by distillation on the basis of 3-methyl-3,4-epoxy-butene-1 used.

EXAMPLES 27 TO 31

Reaction and work up were carried out in the same manner as in Example 18 except that the amine was replaced by those as shown in Table 5. The results are also shown in Table 5.

TABLE 5

| Example | Amine | Molar ratio (A)*1 | Molar ratio (B)*2 | Temperature (°C.) | Yield (%) | Z/E |
|---|---|---|---|---|---|---|
| 27 | DABCO*3 | 1.2 | 1.2 | 0 | 79 | 92.6/7.4 |
| 28 | Triethylamine | 2.6 | 1.3 | 0 | 79 | 93.8/6.2 |
| 29 | N-methylpyrrole | 2.3 | 2.3 | 0 | 89 | 90.5/9.5 |
| 30 | Cyclohexylamine | 1.8 | 4.7 | −20 | 78 | 90.4/9.6 |
| 31 | Morpholine | 2.3 | 3.4 | 0 | 64 | 90.5/9.5 |

Note:
*1 The molar ratio (A) refers to that of amine to 3-methyl-3,4-epoxybutene-1.
*2 The molar ratio (B) refers to that of n-butyllithium to 3-methyl-3,4-epoxy-butene-1.
*3 DABCO, 1,4-diazabicyclo[2,2,2]octane.

EXAMPLES 32 TO 34

Reaction and work up were carried out in the same manner as in Example 18 except that n-butyllithium was replaced by other organolithium compounds as shown in Table 6. The results are also shown in Table 6.

TABLE 6

| Example | Organolithium compound | Amine | Molar ratio*1 | Solvent | Temperature (°C.) | Yield (%) | Z/E |
|---|---|---|---|---|---|---|---|
| 32 | sec-Butyllithium | TMEDA | 1.0 | Hexane | 0 | 74 | 89.4/10.6 |
| 33 | β-Phenethyllithium | TMEDA | 2.0 | Ether | −20 | 59 | 97.7/2.3 |
| 34 | n-Octyllithium | TMEDA | 2.0 | Hexane | −20 | 55 | 95.6/4.4 |

Note:
*1 The molar ratio refers to that of TMEDA to organolithium compound.

NMR spectrum (CDCl$_3$) δ ppm of 6-phenyl-2-methyl-2-hexen-1-ol: Z-isomer: 7.22 (5H, singlet), 5.32 (1H, triplet), 4.06 (2H, singlet), 2.70 (2H, triplet), 2.2−1.1 (8H, multiplet).

EXAMPLE 35

A solution of 258 mg of TMEDA in 1 ml of hexane was cooled to 0° C., and a hexane solution of n-butyllithium (1.1 mmol) was added dropwise thereto under a nitrogen atmosphere and stirred at 0° C. To the resultant mixture, there was added dropwise 1 ml of a hexane solution of 3,4-epoxy-butene-1 (1 mol/liter). After completion of the addition, the resultant mixture was stirred at 0° C. for 1 hour and at room temperature for 30 minutes, followed by the usual work up. After removal of the solvent, the residue was distilled to give 41 mg of 2-octen-1-ol as a colorless oily product (yield, 32%). After acetylation of the thus obtained product, gas chromatographic analysis (PEG 20M, 45 m) was effected at a temperature of 130° C. The Z/E ratio was 76.8/23.2.

EXAMPLES 36 AND 37

Reaction and work up were carried out in the same manner as in Example 15 except that the organolithium and the reaction conditions shown in Table 7 were applied. The results are also shown in Table 7.

TABLE 7

| Example | Organolithium compound | Amine | Molar ratio*1 | Temperature (°C.) | Yield (%) | Z/E |
|---|---|---|---|---|---|---|
| 36 | n-Butyllithium | TMEDA | 2 | −30 | 25 | 76.3/23.7 |
| 37 | sec-Butyllithium | TMEDA | 2 | −20 | 28 | 67.4/32.6 |

Note:
*1 The molar ratio refers to that of TMEDA to organolithium compound.

EXAMPLE 38

A solution of 90 mg of 3-methyl-3,4-epoxybutene-1 in hexane was added dropwise to a hexane solution of n-butyllithium (1.3 mmol) at 0° C. under a nitrogen atmosphere. The mixed solution was stirred at 0° C. for 3 hours and at room temperature for 1 hour. The reaction mixture was recooled to 0° C., and after adding aqueous ammonium chloride solution thereto, extracted with ether. The ether layer was separated, washed with saturated sodium chloride solution and dried over anhydrous magnesium sulfate. Removal of the ether under reduced pressure gave 116 mg of 2-methyl-2-octen-1-ol (yield, 76%; Z/E=87.9/12.1).

EXAMPLES 39 TO 46

Reaction and work up were carried out in the same manner as in Example 38 except that the reaction temperature, the solvent and the molar ratio of feed were varied. The results are shown in Table 8.

TABLE 8

| Example | Molar ratio*1 | Solvent | Temperature (°C.) | Yield*2 (%) | Z/E |
|---|---|---|---|---|---|
| 39 | 1.1 | Ether | 20 | 82 | 84.1/15.9 |
| 40 | 1.1 | Ether | −30 | 70 | 77.3/22.7 |
| 41 | 1.1 | Ether | −78 | 87 | 76.2/23.8 |

TABLE 8-continued

| Example | Molar ratio*1 | Solvent | Temperature (°C.) | Yield*2 (%) | Z/E |
|---|---|---|---|---|---|
| 42 | 1.5 | Heptane | −30 | 99 | 76.2/23.8 |
| 43 | 1.5 | Tetrahydrofuran | −30 | 62 | 76.2/23.8 |
| 44 | 1.1 | Benzene | 4 | 83 | 68.7/31.3 |
| 45 | 1.1 | 1,2-Dimethoxyethane | 0 | 74 | 77.3/22.7 |
| 46 | 1.1 | Toluene | 0 | 88 | 65.5/34.5 |

Note:
*1 The molar ratio refers to that of n-butyllithium to 3-methyl-3,4-epoxybutene-1.
*2 The yield refers to that of 2-methyl-2-octen-1-ol on the basis of 3-methyl-3,4-epoxybutene-1 used.

EXAMPLE 47

Reaction and work up were carried out in the same manner as in Example 38 except that n-butyllithium was replaced by n-hexyllithium in ether. The yield of 2-methyl-2-decen-1-ol was 99%. The Z/E ratio of this product was 83.6/16.4.

NMR spectrum (CDCl$_3$) δ ppm: Z-isomer: 5.30 (1H, triplet), 4.10 (2H, singlet), 2.65 (1H, singlet), 1.80 (3H, singlet), 2.2–0.7 (15H, multiplet); E-isomer: 5.42 (1H, triplet), 3.97 (2H, singlet), 2.65 (1H, singlet), 1.67 (3H, singlet), 2.2–0.7 (15H, multiplet).

EXAMPLE 48

A solution of 97 mg of 3-methyl-3,4-epoxybutene-1 in ether was cooled to −30° C. under a nitrogen atmosphere, and a pentane solution of sec-butyllithium (1.4 mmol) was added dropwise thereto. After stirring at −30° C. for 2.5 hours, the reaction mixture was gradually warmed to room temperature, re-cooled with ice-water, admixed with aqueous ammonium chloride solution and extracted with ether. The ether extract was washed with saturated sodium chloride solution and dried over anhydrous magnesium sulfate. Removal of the ether under reduced pressure gave 103 mg of 2,5-dimethyl-2-heptan-1-ol (yield, 63%; Z/E=86.3/13.7).

EXAMPLES 49 TO 52

Reaction and work up were carried out in the same manner as in Example 48 except that sec-butyllithium was replaced by other organolithium compounds. The results are shown in Table 9.

TABLE 9

| Example | Organolithium compound | Solvent | Temperature (°C.) | Yield (%) | Z/E |
|---|---|---|---|---|---|
| 49 | iso-Butyllithium | Ether | −30 | 65* | 80.8/19.2 |
| 50 | Cyclohexyllithium | Ether | −30 | 55* | 89.0/11.0 |
| 51 | Cyclopropyllithium | Ether | −30 | 77 | 81.5/18.5 |
| 52 | β-Phenylethyllithium | Ether | −30 | 79* | 82.8/17.2 |

*Yield of products isolated after purification by column chromatography or thin layer chromatography (TLC).

NMR spectrum (CDCl$_3$) δ ppm:
2,6-Dimethyl-2-hepten-1-ol:
Z-isomer: 5.33 (1H, triplet, J=7.5 hz), 4.17 (2H, singlet), 2.43 (1H, singlet), 2.3−1.1 (8H, multiplet), 1.05 (6H, doublet, J=6 Hz); E-isomer: 5.45 (1H, triplet) 4.03 (2H, singlet), 2.43 (1H, singlet), 2.3−1.1 (8H, multiplet), 1.05 (6H, doublet, J=6 Hz).

4-Cyclohexyl-2-methyl-2-buten-1-ol:
Z-isomer: 5.42 (1H, triplet), 4.17 (2H, singlet), 2.3−0.6 (17H, multiplet).

4-Cyclopropyl-2-methyl-2-butene-1-ol:
Z-isomer: 5.42 (1H, triplet), 4.12 (2H, singlet), 2.2–1.6 (6H, multiplet), 0.9–0 (5H, multiplet).

What is claimed is:

1. A process for preparing 1,4 adducts exclusively and regioselectively which are predominantly Z-substituted allylic alcohols of the formula:

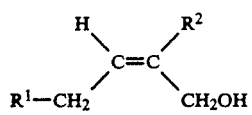

wherein R$^1$ is a straight or branched C$_2$–C$_{25}$ alkyl or C$_3$–C$_{25}$ cycloalkyl group optionally bearing at least one substituent selected from the group consisting of phenyl, naphthyl, lower alkoxy and alkylenedioxy and R$^2$ is a hydrogen atom or a methyl group, which comprises reacting 1 mole of vinyl epoxide of the formula:

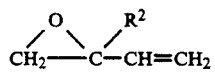

wherein R$^2$ is as defined above with 0.1 to 10 moles of an organolithium compound of the formula:

wherein R$^1$ is as defined in an inert solvent at a temperature of −78° C. to the reflux temperature of the reaction mixture.

2. The process of claim 1, wherein R$^1$ is a C$_{10}$ polycyclic hydrocarbon group.

3. The process according to claim 2, wherein the polycyclic hydrocarbon group is (2,3-dimethyltricyclo [2.2.1.0$^{2,6}$]heptyl-3-)methyl.

4. The process according to claim 2, wherein the polycyclic hydrocarbon group is (2-methyl-3-methylene-norbornyl-2-)methyl.

5. The process according to claim 2, wherein the polycyclic hydrocarbon group is 2,2-lower alkylene-dioxy-1, 7-dimethylbicyclo [2.2.1]heptyl-7-methyl.

6. The process according to claim 1, wherein the reaction is carried out in the precence of a base.

7. The process according to claim 6, wherein the base is an amine.

8. The process according to claim 6, wherein the base is a metal alkoxide.

9. The process according to claim 1, wherein the reaction is carried out at a temperature of −30° to 30° C.

10. A process for preparing 1,4 adducts exclusively and regioselectively which are predominantly Z-substituted allylic alcohols of the formula:

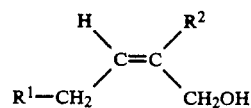

wherein $R^1$ is a straight or branched $C_2$–$C_{25}$ alkyl group and $R^2$ is a hydrogen atom or a methyl group, which comprises reacting 1 mole of a vinyl expoxide of the formula:

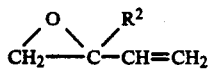

wherein $R^2$ is as defined above with 0.1 to 10 moles of an organolithium compound of the formula:

$$R^1-Li$$

wherein $R^1$ is as defined above in an inert solvent at a temperature of $-78°$ C. to the reflux temperature of the reaction mixture.

11. The process according to claim 10, wherein the reaction is carried out at a temperature of $-30°$ to $30°$ C.

12. The process according to claim 1, wherein $R^1$ is a straight or branched $C_2$–$C_{15}$ alkyl or $C_3$–$C_{25}$ cycloalkyl group optionally bearing at least one substituent selected from the group consisting of phenyl, naphthyl, lower alkoxy, and alkylenedioxy.

13. The process according to claim 10, wherein $R^1$ is a straight or branched $C_2$–$C_{15}$ alkyl group.

14. The process according to claim 1, wherein $R^1$ has a substituent selected from the group consisting of phenyl and ethylenedioxy.

15. The process according to claim 12, wherein $R^1$ has a substituent selected from the group consisting of phenyl and ethylenedioxy.

* * * * *